United States Patent [19]

Scharlack

[11] Patent Number: 5,828,445
[45] Date of Patent: Oct. 27, 1998

[54] METHOD FOR MEASURING AND REPORTING CO-OXIMETER QUALITY CONTROL RESULTS

[75] Inventor: Ronald S. Scharlack, Brookline, Mass.

[73] Assignee: Chiron Diagnostics Corporation, East Walpole, Mass.

[21] Appl. No.: 413,563

[22] Filed: Mar. 30, 1995

[51] Int. Cl.⁶ .............................. G01J 3/42; G01N 33/49
[52] U.S. Cl. .......................... 356/40; 356/300; 356/319; 356/41; 364/498; 364/571.02
[58] Field of Search ................................ 356/40–41, 300, 356/319, 326, 328; 364/571.02, 498

[56] References Cited

U.S. PATENT DOCUMENTS

| | | | |
|---|---|---|---|
| 4,945,062 | 7/1990 | Chiang | 436/11 |
| 5,243,546 | 9/1993 | Maggard | 364/571.02 |

FOREIGN PATENT DOCUMENTS

| | | |
|---|---|---|
| WO92/22804 | 12/1992 | WIPO . |
| WO93/03341 | 2/1993 | WIPO . |

OTHER PUBLICATIONS de Noord, Onno E., "Multivariate Calibration Standardization", *Chemometrics and Intelligent Laboratory Systems*, 25 (1994) 85–97.

Lorber, Avraham, et al., "Estimation of Prediction Error for Multivariate Calibration", *Journal of Chemometrics*, vol. 2, (1988) 93–109.

Wang, Yongdong, et al., "Multivariate Instrument Standardization", *Analytical Chemistry*, vol. 63, No. 23, (Dec. 1, 1991), 2750–2756.

*Primary Examiner*—F. L. Evans
*Attorney, Agent, or Firm*—Arthur S. Morgenstern; Charles L. Gagnebin, III; Robert P. Blackburn

[57] ABSTRACT

The present invention comprises methods of determining the performance of an absorbance spectrometer, and, in particular, of CO-oximeters. The methods comprise measuring the absorbance spectrum of a quality control sample and comparing it to a standard spectrum of that quality control. Instrumental error will be the primary factor contributing to the observed difference. The present method also provides techniques for converting the instrumental error manifested in the difference between the measured and standard quality control spectra into blood concentration values comparable to that of real blood. Analysis of test samples on a spectrophotometer; and calibration of the spectrophotometer is also provided.

17 Claims, 5 Drawing Sheets

METHOD FOR MEASURING AND REPORTING CO-OXIMETER QUALITY CONTROL RESULTS

FIELD OF THE INVENTION

This invention relates to the field assessing the performance of spectrophotometers.

SUMMARY OF THE RELATED ART

Ultraviolet-visible-infrared (UV-VIS-IR) absorbance spectroscopy has become an invaluable tool in medical diagnostics and analytical chemistry. For example, CO-oximeters measure the concentrations of various hemoglobin components or fractions in physiological blood using absorption spectroscopy. CO-oximeters perform this function by measuring the VIS-IR absorbance spectrum of a blood sample and determining the best fit of known blood component spectra.

It is easily appreciated, therefore, that it is important to be able to quickly and accurately determine instrument performance. Existing methods measure the absorbance spectrum of quality control products. QC products specific for blood analysis are typically red dye based samples constructed to simulate the spectrum of blood. In addition to a red dye, they sometimes contain certain amounts of oxygen, carbon dioxide, and electrolytes at an established pH for determining the performance of blood gas and electrolyte instruments. It is very difficult to construct QC products having an absorbance spectrum that closely mimics that of physiological blood.

Standard blood component spectra are used to obtain the best fit to the measured QC product spectrum. By varying the contributions of each blood component spectrum, a best fit to the QC spectrum is obtained. But because even the ideal QC spectrum does not mimic that of physiological blood well, the resulting best fit deviates from the observed QC spectrum even when the instrument is running perfectly. Furthermore, instrument introduced errors are not reported in terms easily understood by the ordinary technician operating the instrument. For example, current methods report the fraction of the major blood components (as determined from the relative contribution of each blood component's spectrum to the best fit spectrum). Quite often a fractional concentration of a blood component is negative. Consequently, improved methods of determining and reporting instrument performance are desired.

SUMMARY OF THE INVENTION

The present invention provides methods of determining and reporting the performance of VIS-IR spectrophotometers used to measure the concentration of hemoglobin components or fractions in blood samples. In particular, the method is used to determine the performance of CO-oximeters. In one aspect of the invention, the methods comprise measuring the absorbance spectrum of a quality control product (QC product) sample and comparing it to the known, standard spectrum for the same QC product. The known standard spectrum of the QC product is obtained from a well calibrated, highly precise spectrophotometer under controlled conditions and electronically stored in the instrument by the manufacturer for future comparison. The QC sample spectrum measured in commercial analytical instruments will differ from the standard spectrum primarily do to various instrumental errors. The standard spectrum is mathematically fit to the measured spectrum, yielding an apparent concentration of the QC. The difference between the measured spectrum and the best fit standard spectrum (the "error spectrum") and the variance of the apparent QC concentration from the standard QC concentration is a measure of the instrumental error.

One important use of the foregoing method is to gauge the performance of spectrophotometers used for analytical determinations including the concentration of various blood components. This method of determining instrumental performance is easily conducted by the technician at the laboratory site and involves simply measuring the absorbance spectrum of a QC sample. The instrument can be programmed to automatically carry-out the foregoing procedure and report the instrumental error. If the observed instrumental error is too large, the instrument may need to be serviced before analysis of test samples.

This method is distinguishable from prior art methods because the measured spectrum closely resembles the standard spectrum to which it is compared. Furthermore, this method also allows the results to be reported in terms readily recognized and easily appreciated by the technician.

In another aspect of the present invention, the concentration of the QC obtained from the mathematical fit is converted into a total apparent hemoglobin concentration ($T_{app}$). This is accomplished by multiplying the apparent concentration of the QC by a nominal value of the total hemoglobin concentration ($T_{nom}$), which, in one aspect of the invention, is equal to the normal level of hemoglobin found in human blood. $T_{app}$ is the total hemoglobin concentration one would have determined from the absorption spectrum of a test sample having a hemoglobin concentration of $T_{nom}$. This number is easily appreciated by the technician, and, if it differs too much from the nominal concentration of human hemoglobin, will indicate to the technician that the instrument may need servicing.

In another aspect, the QC spectrum and spectral measurement errors are conveniently translated into concentrations of blood components, i.e. hemoglobin fractions and lipid. This allows for ready recognition and appreciation of the QC results by technicians. This may be accomplished in one of two ways. The simplest way is to multiply the total apparent hemoglobin concentrations ($T_{app}$) by a nominal fraction of each component in blood. The nominal fractions are preferably the fraction of the total hemoglobin concentration of the particular component (e.g., oxygenated hemoglobin) normally found in physiological blood. This method presents the same information contained in $T_{app}$, but in a different format.

The second, more preferred method of determining and reporting fractional blood component concentrations uses a mathematical analysis to determine the errors in concentrations of the major blood components due to instrumental errors. This method determines the values of the blood component concentrations that would give rise to the error spectrum. Several blood component spectra are mathematically combined to give the best fit to the error spectrum. The contributions of each blood component spectrum directly yield the concentration of the blood component. These concentrations are the deviations (owing to instrumental error) from the actual concentrations of these components that one would observe if an actual blood sample were analyzed. Adding these concentrations to the nominal concentrations of the blood components yields the concentrations of the blood components that would have been observed if a blood sample having the nominal concentrations of blood components were analyzed on the instrument.

In a preferred embodiment, the nominal values of blood component concentrations are set to those values observed in normal human blood. The significance of the results then can be readily appreciated by the ordinary technician. If the errors are beyond acceptable limits, servicing may be required.

The present method provides an improved ability to determine the performance of the instrument, because the measured QC sample spectrum more closely resembles the known, standard spectrum. The result is that the measured errors more directly relate to the instrument errors. Concomitantly, the difficult task of formulating stable QC products that mimic blood spectra is eliminated. Furthermore, one can use the same QC product on instruments using different wavelengths for measurement parameters and retain the ability to report the results at the same nominal value. These nominal values can be advantageously set to any desired value.

The present method further provides the ability to scale the concentration of blood components to better reflect anticipated instrument variations when physiological blood samples are run.

The foregoing merely summarizes certain aspects of the invention and is not intended, nor should it be construed, to limit the invention in any way.

DETAILED DESCRIPTION OF THE PREFERRED EMBODIMENTS

The present invention provides a new method for determining the performance level of an absorbance spectrophotometer. As used herein, the terms "absorbance spectrometer," "spectrometer," and their equivalents mean any machine or instrument capable of measuring the absorbance spectrum of a liquid sample. The present methods are particularly useful for determining the performance of CO-oximeters.

The methods comprise measuring the absorbance spectrum of a quality control (QC) sample and evaluating the quality of the fit to the known, standard spectrum for that QC product. The difference between the two is a measure of the performance of the spectrophotometer.

Figure 3:
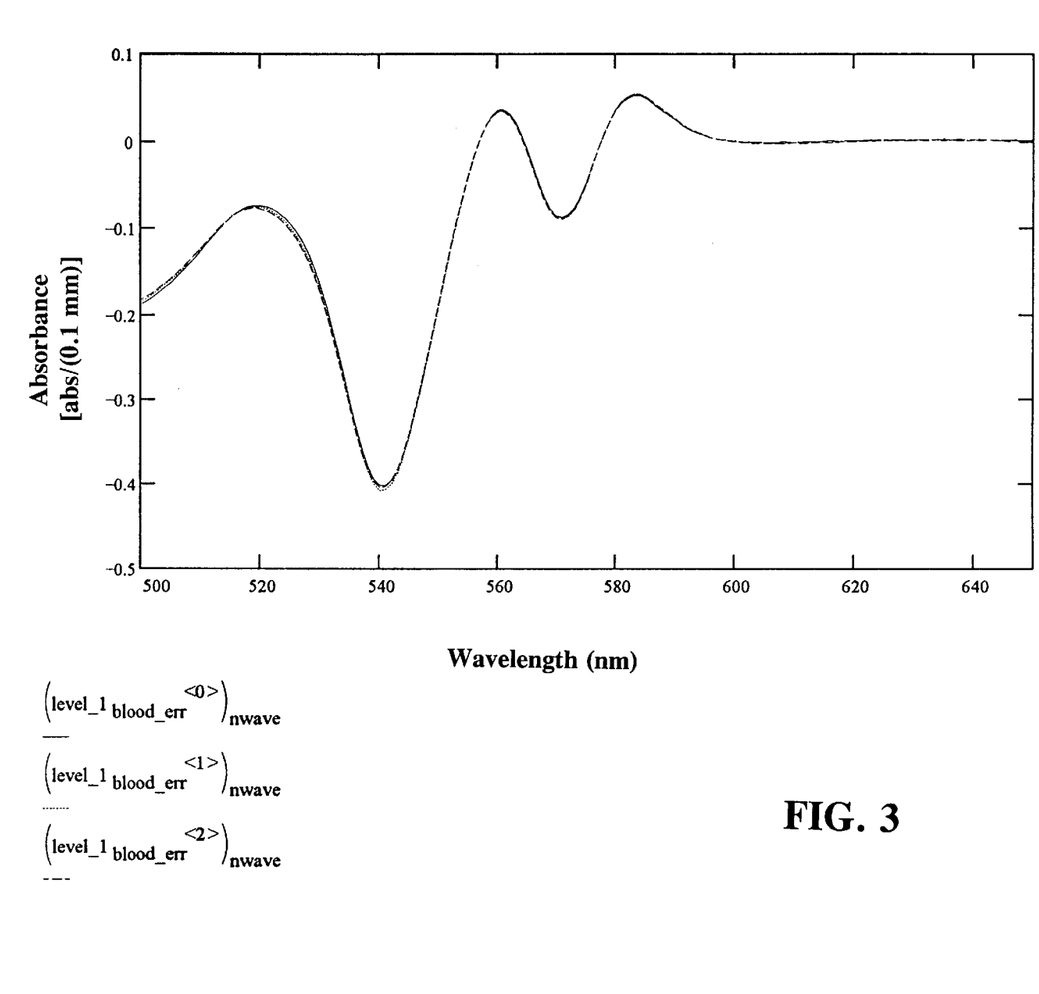
FIG. 3 displays the spectra that are the difference between the QC spectra of FIG. 1 and the least squares best fit to those spectra using the blood component spectra of FIG. 2.
Figure 4:
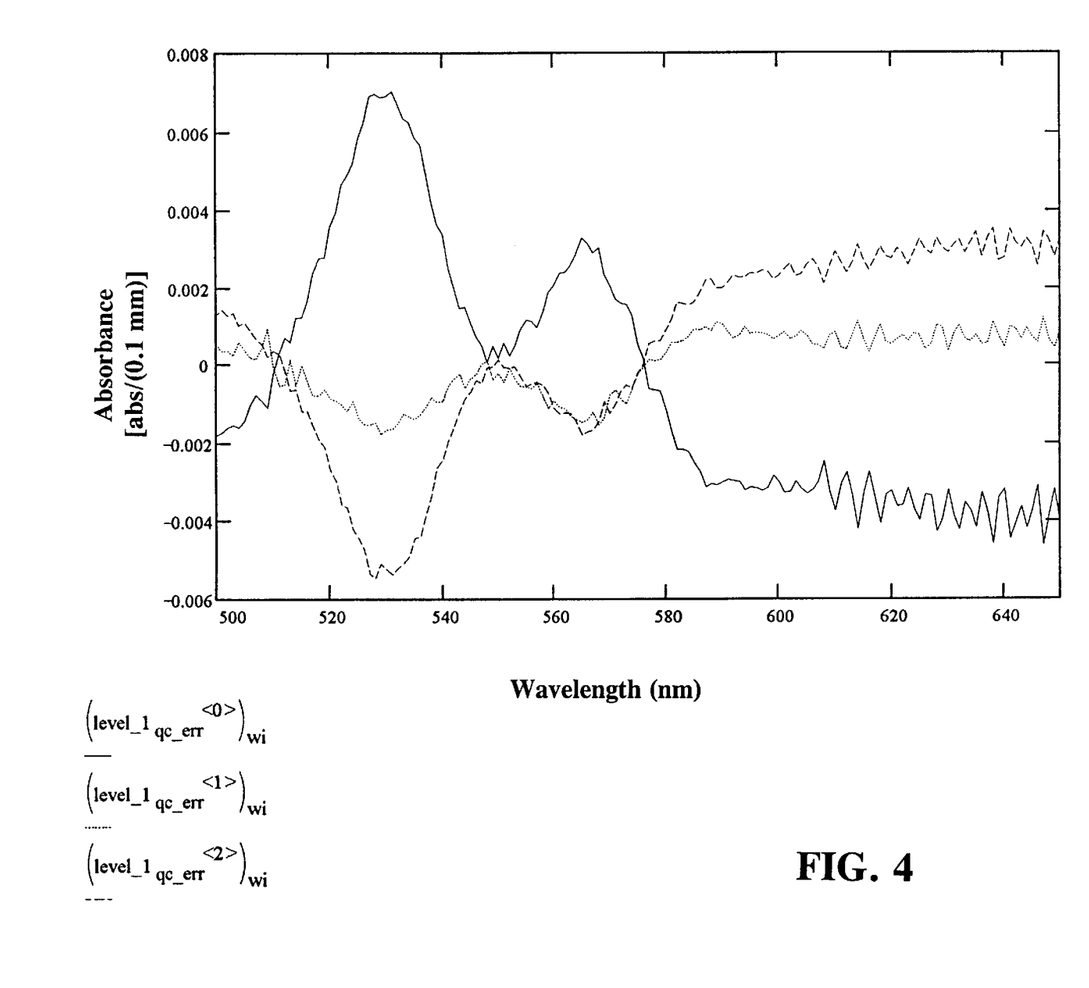
FIG. 4 displays the error spectra, i.e., the difference between the measured QC spectra of FIG. 1 and the least squares best fit standard QC, which in this case is the average of the three QC spectra of FIG. 1.
Figure 5:
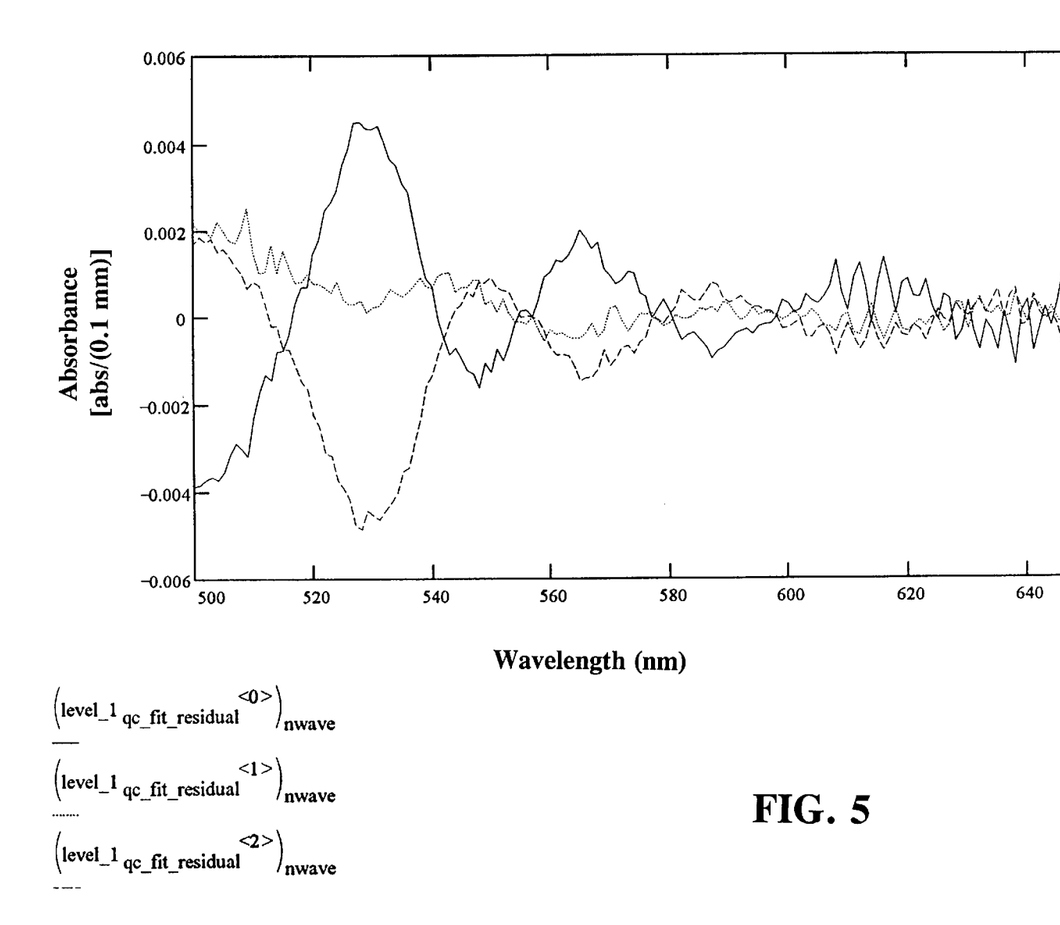
FIG. 5 displays the spectra that are the difference between the error spectrum of FIG. 4 and the least squares best fit to those spectra using the blood component spectra of FIG. 2.

This method is distinguishable from prior art methods, which compare measured QC spectra to a standard blood spectrum. Because the QC spectra do not mimic blood spectra well, the observed differences in the measured QC spectrum and a standard blood spectrum are rather large (FIG. 3) and arise due to both variations on instrument performance as well as the inherent differences in the two spectra. The present methods improve upon this by greatly reducing or eliminating the inherent difference between the measured QC sample spectrum and the standard spectrum to which it is compared. FIGS. 3 and 4.

A shortcoming of the prior art is that blood component concentrations obtained from QC spectra often bear little or no relation to real values in blood, often appearing as negative concentrations or concentrations of greater than 100%. The present methods improve upon the prior art in that the instrumental error can be reported in terms of blood component concentrations that are comparable to real values in blood, and thus easily understandable to the technician in the field.

The inventive method is based on the well known Beer-Lambert law:

$$A_\lambda = q_\lambda \cdot c \cdot x \tag{1}$$

where A is the absorbance at wavelength $\lambda$, $q_\lambda$ is the extinction coefficient at wavelength $\lambda$ for the absorbent, c is the concentration of the absorbent, and x is the sample path length through which the measuring beam of light passes. The path length x is constant within the spectrophotometer (typically expressed in cm) and hereinafter will be subsumed in $q_\lambda$.

If there are "n" components in the sample, the Beer-Lambert law can be expressed in linear algebraic terms as:

$$A = q \cdot c, \tag{2}$$

where A is a vector whose "m" elements $A_{\lambda,i}$ are the absorbencies at "m" discrete wavelengths $\lambda_i$, q is an "m×n" matrix whose elements $q_{ij}$ are the extinction coefficients of component "j" at wavelength $\lambda_i$, and c is a vector, each of whose "n" elements $c_j$ is the concentration of component "j".

Figure 1:
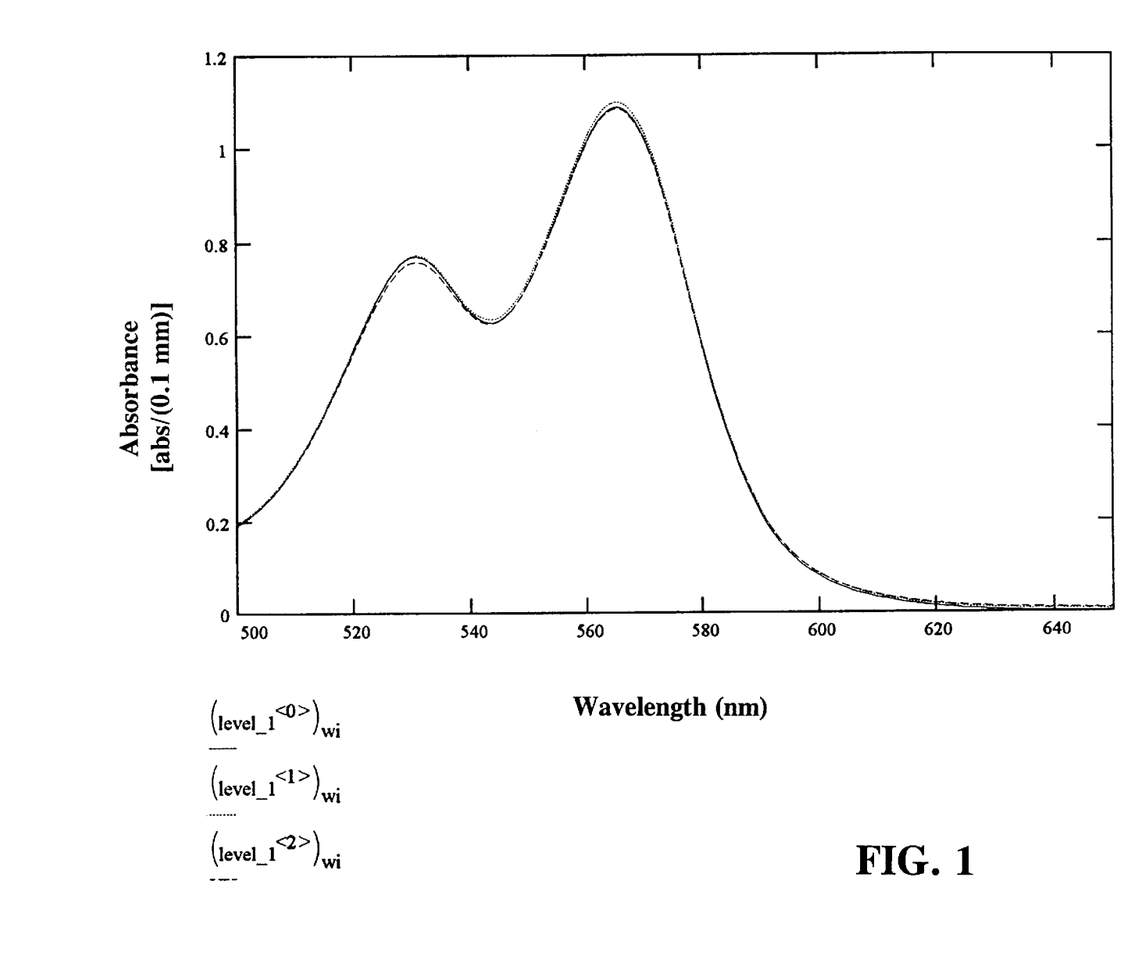
FIG. 1 displays three QC spectra of the three lots of CERTAIN® ELITE Level 1 QC product of Example 1.

In the present invention, the absorbance spectrum ($A_{meas}$) of a QC sample is measured (FIG. 1). The QC sample has a known set of extinction coefficients q as determined by measuring the absorbance spectrum or standard spectrum (with concentration $c_{std}$) on a calibrated spectrophotometer. In practice, a standard absorbance spectrum ($A_{std}$) of a QC product will be recorded on a high precision spectrophotometer and the concentration ($c_{std}$) arbitrarily set to unity so that $q = A_{std}$. Alternatively, the standard QC spectrum may be obtained by averaging two or more QC sample spectra. The QC samples used to determine instrument performance are manufactured to be identical (i.e., have the same $c_{std}$) to the QC product used to obtain $A_{std}$. It is noted that variation in the product specifications of different lots of QC products may impact the analysis, although this variation should be minor. The vector q is then electronically stored in the instrument by the manufacturer for use in future determinations of instrument performance.

The QC spectra will generally differ from the samples (e.g., blood samples) that are commonly analyzed on the spectrophotometer. As used herein, the term "analyze" means to determine the identity and/or concentration of component(s) of a sample. To give the most accurate and meaningful indication of instrument performance, the QC sample should preferably be constructed to give an absorbance spectrum closely mimicking that of samples frequently analyzed on the spectrophotometer. In a preferred embodiment, the QC sample will mimic human blood. QC products suitable for use in the invention are commercially available, for example, from Ciba Corning Diagnostics Corp. (Medfield, Mass.) under the trade name CERTAIN® ELITE.

The standard QC spectrum, $A_{std}$, is fit to the measured spectrum, $A_{meas}$, by treating "c" in equation (2) as a variable and determining the value of "c" that results in the best fit. The result is an apparent concentration of the QC, $c_{app}$. A variety of potential sources of instrumental error will result in $A_{meas}$ differing from $A_{std}$ and, consequently, $c_{app}$ differing from $c_{std}$. Any of the well known mathematical techniques of fitting spectra can be used to determine the best fit of $A_{std}$ to $A_{meas}$ and from it $c_{app}$. See Press et al., *Numerical Recipes: The Art of Scientific Computing* Ch. 14, pp. 498–546 (Cambridge University Press, Cambridge, 1986). In a preferred embodiment, $c_{app}$ is obtained by a least squares analysis and is given by:

$$c_{app} = (q^T q)^{-1} q^T \cdot A_{meas}. \tag{3}$$

See Noble and Daniel, *Applied Linear Algebra*, pp. 57–65 (Prentice-Hall 1977). The apparent concentration, $c_{app}$, can then be used to give the estimated, best fit (in the least squares sense) absorbance spectrum, $A_{est}$:

$$A_{est} = q \cdot c_{app}. \tag{4}$$

The difference between the measured and estimated absorbance spectra at each wavelength, i.e., the "error spectrum" is given by the vector E:

$$E = A_{est} - A_{meas}. \tag{5}$$

(FIG. 4). The vector E is a measure of the deviation of instrumental performance from the ideal.

It is difficult to determine from E itself, however, the level of instrument performance and whether the instrument is performing within acceptable standards. In a preferred embodiment of the present invention, E is advantageously related to errors in the measured concentration of blood components ($C_{\Delta Hb}$) that would result from the instrumental errors. $C_{\Delta Hb}$ is a vector having "k" elements, each being the error in concentration of one of the blood components. $C_{\Delta Hb}$ is the vector of blood component concentrations that would give rise to the observed error spectrum, E. $C_{\Delta Hb}$ can be determined in a variety of ways involving fitting the error spectrum with one or more known blood component spectra by varying the intensities of each blood component spectrum. The relative contributions of each of the blood component spectrum are the relative concentrations of each of the components. Preferably, the least squares method is used. If $Q_{Hb}$ is the "k×m" matrix of extinction coefficients for "k" blood components at "m" wavelengths, then $C_{\Delta Hb}$ is given by:

$$C_{\Delta Hb} = (Q_{Hb}^T Q_{Hb})^{-1} Q_{Hb}^T \cdot E. \tag{6a}$$

or $$C_{\Delta Hb} = W \cdot (Q_{Hb}^T Q_{Hb})^{-1} Q_{Hb}^T \cdot E. \tag{6b}$$

The $C_{\Delta Hb}$ thus obtained will have the same units as $Q_{Hb}$, preferably gm/dL. The values of $C_{\Delta Hb}$ can be positive (indicating that the instrumental errors would result in measured blood component concentrations that are too high) or negative (indicating that instrumental error would result in measured blood component concentrations that are too low). If all elements of E were zero, i.e., $A_{meas} = A_{std}$, meaning the instrument was performing ideally, there would be no error in the measurements of the concentrations of blood components, and all elements of $C_{\Delta Hb}$ would be zero.

Weight or W is a matrix which scales the concentration of blood components to better reflect anticipated instrument variations when physiological blood samples are run. The simplest case is when the diagonal elements equal 1 and the others are 0.

Equation 6b provides a transformation of the error concentrations obtained with QC so that they reflect values that would have been obtained if the sample was oxyhemoglobin. A physiological sample transformation is a matrix which weights each fraction of error to adjust it to a new value. Errors due to instrument inaccuracies, such as spectral or wavelength shift, result in characteristic errors for each hemoglobin fraction as well as each quality control. The characteristic response of the instrument to such inaccuracies can be predetermined for any specific sample. Since physiological samples are predominantly oxyhemoglobin and since the characteristic response of the instrument (due to inaccuracies) will be different for samples other than oxyhemoglobin, it is desirable to compensate for these differences.

In another preferred embodiment of the invention, the total concentration of hemoglobin is reported ($T_{app}$). It is the product of the apparent concentration of the QC measured, $c_{app}$, and the nominal value of total hemoglobin, $T_{nom}$:

$$T_{app} = T_{nom} \cdot c_{app}. \tag{7}$$

$T_{nom}$ can be set to any convenient value. In a preferred embodiment, $T_{nom} = 14$ g/dL, a value typical of normal human blood. Thus, if $c_{app} = 1$ (which is the arbitrary value chosen for the QC product and would result if $A_{meas} = A_{std}$), the reported total hemoglobin would be the same as that observed in normal human blood.

The nominal concentration of the "k" blood components, $C_{nom}$, is given by:

$$C_{nom} = F_{nom} \cdot T_{nom}, \tag{8}$$

where $F_{nom}$ is the vector each of whose elements $F_{nom,i}$ are the nominal fractions of blood component "i." In a preferred embodiment of the present invention, the elements of $F_{nom}$ are set to the actual fractions of the blood components observed in human blood.

The apparent concentration of blood components that one would observe on the instrument being tested ($C_{Hb,app}$) is the sum of the nominal concentrations ($C_{nom}$) and the errors in blood component concentrations previously calculated, $C_{\Delta Hb}$:

$$C_{Hb,app} = C_{nom} + C_{\Delta Hb}. \tag{9}$$

The total calculated hemoglobin concentration (the scalar $T_{calc}$) is the sum of the calculated values of the components, i.e., the sum of the elements of the vector $C_{Hb,app}$. The reported fractions of the blood components $F_{rep}$ is then given by:

$$F_{rep} = C_{Hb,app} / T_{calc} \tag{10}$$

Evaluation of any one or more of the foregoing indicia of instrumental performance will allow the field technician to determine whether servicing of the spectrophotometer is required or that test sample analysis may proceed.

That is, one may observe any one or more of the following:

1. the deviation of the best fit quality control spectrum ($A_{est}$) from the measured QC spectrum ($A_{meas}$) or, equivalently, the error spectrum, E;
2. the deviation of $c_{app}$ from $c_{std}$;
3. $C_{\Delta Hb}$;
4. the deviation of $T_{app}$ or $T_{calc}$ from $T_{nom}$;
5. the deviation of $C_{Hb,app}$ from $C_{nom}$;
6. the deviation of $F_{rep}$ from $F_{nom}$; and 7. any equivalent indicium of instrumental performance derived from the comparison of $A_{meas}$ and $A_{std}$.

Acceptable limits within which the instrument is required to perform will depend on the particular circumstances and will vary from application to application. For instance, in cases where only rough estimates of concentrations are needed, a larger deviation of any of the foregoing parameters from the ideal can be tolerated. On the other hand, where extremely precise measurements of concentration are required, only small deviations in the foregoing parameters will be acceptable. Typical acceptable values will vary within about±2% of the nominal value.

The major components of blood that will ordinarily be used in the present methods are reduced hemoglobin (HHb), oxygenated hemoglobin ($O_2$Hb), carboxy hemoglobin (COHb), met hemoglobin (MetHb), sulf hemoglobin (SHb), and lipid. The extinction coefficients for hemoglobin-based blood components can be measured directly or obtained from the literature. See Zijlstra et al., *Clin. Chem.* 37(9), 1633–1638 (1991). The lipid spectrum can be measured from intravenous fat emulsion (e.g., the commercially available lipid product LIPOSYN™ II) in an aqueous dispersion of about 10% by weight.

Any number of wavelengths can be used to measure and fit the foregoing spectra, but at a minimum there must be at least as many wavelengths as there are variables (i.e., concentrations) to be fit. The larger the number of wavelengths used, the less contribution there will be from random noise and, therefore, the more accurate the measurements. As a practical matter, seven wavelengths can be used to fit an error spectrum with 6 component spectra, e.g., HHb, $O_2$Hb, COHb, MetHb, SHb, and lipid. Preferably the spectra are measured and fit at wavelengths at which the QC products have at least a moderate level of absorbance.

The following examples are offered for illustrative purposes only and are not intended, nor should they be construed, to limit the invention in any manner.

EXAMPLES

Example 1

The methods of the present invention were applied to three different lots of three different CERTAIN® ELITE (Ciba Corning Diagnostics, Medfield, Mass.) QC products, Levels 1, 2, and 3. In this Example, the standard QC spectrum was obtained by averaging the QC sample spectra of the three lots 1–3 at each level. Accordingly, the deviations observed in this Example arise from differences in the QC sample lots. The deviations from the standard spectrum, however, are representative of deviations one would observe from instrumental errors.

Absorbance spectra were obtained on a CARY IV (Varian Instruments, Palo Alto, Calif.) and are displayed in FIG. 1 for QC Level 1 lots 1–3. The error spectra were fit at seven wavelengths in the range of 550–650 nm using absorbance spectra of HHb, MetHb, $O_2$Hb, COHb, SHb, and lipid. The reported results for the present method were calculated using the methods described above. The results are displayed below. As can be seen, the values for the concentrations of blood components calculated using the present method correspond to values one might observe for real blood. By contrast, the values of blood component concentrations using prior art methods can be negative or greater than 100% of the total hemoglobin.

QC LEVEL 1-$T_{nom}$ = 11.5 gm/dL
Mean QC Concentration

|  | Lot 1 | Lot 2 | Lot 3 |
|---|---|---|---|
| Concentration ($C_{app}$) | 0.995 | 1.009 | 0.996 |
| Concentration error | −0.005 | 0.009 | −0.004 |

Blood Component Concentration Errors

|  | $C_{\Delta Hb,i}$ (gm/dL) | | | ($C_{\Delta Hb,i}/T_{nom}$) × 100% = % Error | | |
|---|---|---|---|---|---|---|
|  | Lot 1 | Lot 2 | Lot 3 | Lot 1 | Lot 2 | Lot 3 |
| HHb | 0.055 | 0.005 | −0.060 | 0.48 | 0.04 | −0.52 |
| $O_2$Hb | −0.016 | 0.012 | 0.003 | −0.14 | 0.10 | 0.03 |
| $CO_2$Hb | 0.040 | −0.031 | −0.009 | 0.35 | −0.27 | −0.08 |
| MetHb | 0.053 | −0.017 | −0.037 | 0.46 | −0.15 | −0.32 |

Reported Results ($F_{nom,i}$ × 100%)

|  | Nominal Value | Present Method | | | Prior Art Method | | |
|---|---|---|---|---|---|---|---|
|  |  | Lot 1 | Lot 2 | Lot 3 | Lot 1 | Lot 2 | Lot 3 |
| HHb | 3 | 3.44 | 3.05 | 2.50 | 2.7 | 2.3 | 1.7 |
| $O_2$Hb | 93 | 91.80 | 93.36 | 93.87 | −22.1 | −22.2 | −22.4 |
| $CO_2$Hb | 2 | 2.32 | 1.73 | 1.94 | 121.3 | 122.6 | 123.4 |
| MetHb | 2 | 2.43 | 1.86 | 1.70 | −1.8 | −2.6 | −2.7 |
| $T_{app,i} = c_{app} \cdot T_{nom,i}$ |  | 11.44 | 11.60 | 11.45 | 11.71 | 11.69 | 11.48 |

QC LEVEL 2-$T_{nom}$ = 17.5 gm/dL
Mean QC Concentration

|  | Lot 1 | Lot 2 | Lot 3 |
|---|---|---|---|
| Concentration ($C_{app}$) | 1.006 | 1.003 | 0.991 |
| Concentration error | 0.006 | 0.003 | −0.009 |

Blood Component Concentration Errors

|  | $C_{\Delta Hb,i}$ (gm/dL) | | | ($C_{\Delta Hb,i}/T_{nom}$) × 100% = % Error | | |
|---|---|---|---|---|---|---|
|  | Lot 1 | Lot 2 | Lot 3 | Lot 1 | Lot 2 | Lot 3 |
| HHb | 0.03 | 0.04 | −0.068 | 0.17 | 0.23 | −0.39 |
| $O_2$Hb | 0.012 | 0.002 | −0.012 | 0.07 | 0.01 | −0.07 |
| $CO_2$Hb | −0.053 | 0.009 | 0.044 | −0.03 | 0.05 | 0.25 |
| MetHb | 0.011 | 0.012 | −0.021 | 0.06 | 0.07 | −0.12 |

Reported Results ($F_{nom,i}$ × 100%)

|  | Nominal Value | Present Method | | | Prior Art Method | | |
|---|---|---|---|---|---|---|---|
|  |  | Lot 1 | Lot 2 | Lot 3 | Lot 1 | Lot 2 | Lot 3 |
| HHb | 3 | 3.00 | 2.99 | 3.01 | 11.7 | 11.7 | 11.1 |
| $O_2$Hb | 93 | 93.23 | 92.96 | 92.8 | −18.5 | −18.5 | −18.7 |
| $CO_2$Hb | 2 | 2.07 | 2.00 | 1.93 | 110.1 | 110 | 110.8 |
| MetHb | 2 | 1.7 | 2.04 | 2.25 | −3.2 | −3.2 | −3.3 |
| $T_{app,i} = c_{app} \cdot T_{nom,i}$ |  | 17.61 | 17.55 | 17.34 | 17.82 | 17.51 | 17.72 |

QC LEVEL 3-$T_{nom}$ = 20.8 gm/dL
Mean QC Concentration

|  | Lot 1 | Lot 2 | Lot 3 |
|---|---|---|---|
| Concentration ($C_{app}$) | 1.011 | 0.987 | 1.002 |
| Concentration error | 0.011 | −0.013 | 0.002 |

Blood Component Concentration Errors

|  | $C_{\Delta Hb,i}$ (gm/dL) | | | ($C_{\Delta Hb,i}/T_{nom}$) × 100% = % Error | | |
|---|---|---|---|---|---|---|
|  | Lot 1 | Lot 2 | Lot 3 | Lot 1 | Lot 2 | Lot 3 |
| HHb | 0.006 | −0.017 | 0.01 | 0.03 | −0.08 | 0.05 |

-continued

|  | | | | | | |
|---|---|---|---|---|---|---|
| O$_2$Hb | −0.017 | −0.01 | 0.027 | −0.08 | −0.05 | 0.13 |
| CO$_2$Hb | −0.01 | 0.071 | −0.06 | −0.05 | 0.34 | −0.29 |
| MetHb | −0.002 | 0.006 | −0.004 | −0.01 | 0.03 | −0.02 |

Reported Results ($F_{nom,i} \times 100\%$)

|  | Nominal Value | Present Method | | | Prior Art Method | | |
|---|---|---|---|---|---|---|---|
|  |  | Lot 1 | Lot 2 | Lot 3 | Lot 1 | Lot 2 | Lot 3 |
| HHb | 3 | 3.00 | 3.00 | 2.99 | 16.1 | 15.9 | 16.1 |
| O$_2$Hb | 93 | 93.05 | 93.12 | 92.83 | −16.7 | −16.6 | −16.5 |
| CO$_2$Hb | 2 | 2.03 | 1.92 | 2.05 | 104.1 | 104.2 | 103.9 |
| MetHb | 2 | 1.92 | 1.95 | 2.13 | −3.5 | −3.4 | −3.5 |
| $T_{app,i} = c_{app} \cdot T_{nom,i}$ |  | 21.03 | 20.53 | 20.84 | 20.81 | 21.05 | 21.03 |

Example 2

Figure 2:
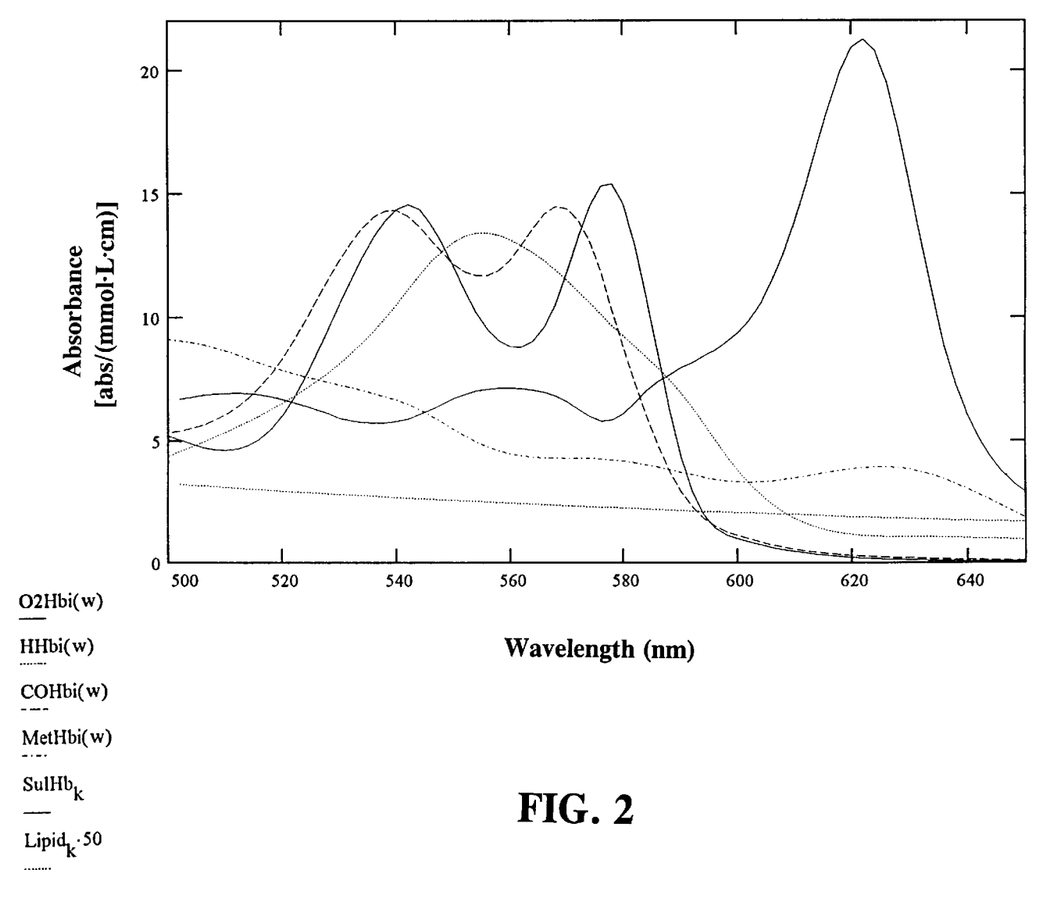
FIG. 2 displays the spectra of the major absorbing blood components.

The QC Level 1, lots 1–3 spectra displayed in FIG. 1 were fit using a least squares analysis by the blood component spectra of FIG. 2. The difference between the best fit and the QC spectra are displayed in FIG. 3. As can be seen, the differences are orders of magnitude larger than the error spectrum obtained by subtracting the best fit QC spectra from the measured QC spectra.

I claim:

1. A method of determining the quality of performance of an absorbance spectrometer, the method comprising:
   a. measuring the absorbance spectrum of a quality control sample;
   b. fitting the measured sample spectrum with the standard spectrum of the quality control sample to obtain a best fit spectrum and an apparent concentration of the quality control sample; and
   c. evaluating the quality of the fit.

2. The method, according to claim 1, wherein the quality of the fit is evaluated by calculating the difference between the best fit spectrum and the measured spectrum to yield an error spectrum.

3. The method, according to claim 1, wherein the quality of the fit is evaluated by determining the deviation of the apparent concentration of the quality control sample, $c_{app}$, from a standard concentration of the quality control sample, $c_{std}$.

4. The method, according to claim 2, wherein a least squares analysis is used to fit the standard spectrum to the measured spectrum.

5. The method, according to claim 3, wherein a least squares analysis is used to fit the standard spectrum to the measured spectrum.

6. The method, according to claim 1, wherein the quality of the fit is evaluated by fitting one or more blood component spectra to an error spectrum to yield errors in concentration of blood components.

7. The method, according to claim 6, wherein a least squares analysis is used to fit the standard spectrum for the quality control sample to the measured spectrum and to fit the one or more blood component spectra to the error spectrum.

8. The method, according to claim 1, wherein the quality of the fit is evaluated by selecting a nominal total concentration of hemoglobin, multiplying the nominal total concentration of hemoglobin by the apparent quality control sample concentration to yield an apparent total hemoglobin concentration.

9. The method, according to claim 8, wherein a least squares analysis is used to fit the standard spectrum for the quality control sample to the measured spectrum.

10. The method, according to claim 6, wherein the quality of the fit is evaluated by selecting nominal values of concentrations of the blood components, adding the errors in concentrations of blood components to their respective nominal concentration values to yield apparent concentrations of the blood components, and evaluating the apparent concentrations of blood components.

11. The method, according to claim 10, wherein a least squares analysis to used to fit the standard spectrum for the quality control sample to the measured spectrum and to fit the one or more blood component spectra to the error spectrum.

12. The method, according to claim 10, wherein the quality of the fit is determined by selecting a nominal total concentration of hemoglobin, multiplying the nominal total concentration of hemoglobin by the apparent quality control sample concentration to yield an apparent total hemoglobin concentration, and dividing the nominal concentrations of hemoglobin components by the apparent total hemoglobin concentration to obtain fractional concentrations of hemoglobin components.

13. The method, according to claim 6, wherein the concentration of blood components are weighted to reflect anticipated instrument variations.

14. The method, according to claim 1, wherein said standard spectrum of the quality control sample has similar connotations of one or more absorbing components of the quality control sample.

15. The method, according to claim 1, further comprising the step of measuring the absorbance spectrum of a test sample.

16. A method of performing absorbance spectrophotometer analysis comprising:
   a. measuring the absorbance spectrum of a quality control product;
   b. fitting the measured spectrum with a standard spectrum of a quality control product having the similar concentration of one or more absorbing components to obtain a best fit spectrum and an apparent concentration of the quality control product;
   c. evaluating the quality of the fit; and
   d. measuring the absorbance spectrum of a test sample.

17. A method for calibrating an absorbance spectrophotometer comprising:
   a. measuring the absorbance spectrum for a plurality of quality control samples, wherein said quality control samples correspond to a blood component spectra;
   b. fitting the measured spectrum with a standard spectrum of a quality control product having the same concentration of absorbing components to obtain a best fit spectrum and an apparent concentration of the quality control samples;
   c. evaluating the quality of the fit; and
   d. adjusting the calibration of said spectrophotometer.

* * * * *